US006292679B1

United States Patent
Sheard

(10) Patent No.: US 6,292,679 B1
(45) Date of Patent: Sep. 18, 2001

(54) LEG PLATE

(76) Inventor: Leonard T. Sheard, 1258 S. Lake Rd., Amherst Junction, WI (US) 54407

( * ) Notice: Subject to any disclaimer, the term of this patent is extended or adjusted under 35 U.S.C. 154(b) by 0 days.

(21) Appl. No.: 09/496,618

(22) Filed: Feb. 2, 2000

(51) Int. Cl.$^7$ ........................................... A61B 5/04
(52) U.S. Cl. .......................... 600/376; 600/391; 600/393
(58) Field of Search .................................. 600/372, 376, 600/382, 384, 386, 391, 393, 395; 607/152

(56) References Cited

U.S. PATENT DOCUMENTS

| | | |
|---|---|---|
| 3,599,628 | 8/1971 | Abbenante et al. . |
| 4,209,020 | 6/1980 | Nielsen . |
| 4,365,634 | 12/1982 | Bare et al. . |
| 4,583,548 | 4/1986 | Schmid . |
| 4,635,642 | 1/1987 | Cartmell et al. . |
| 4,643,193 | 2/1987 | DeMarzo . |
| 4,653,501 | 3/1987 | Cartmell et al. . |
| 4,771,783 | 9/1988 | Roberts . |
| 4,890,622 | 1/1990 | Ferrari . |
| 5,046,965 * | 9/1991 | Neese et al. .......................... 600/376 |
| 5,062,426 | 11/1991 | Ulbrich et al. . |
| 5,168,876 * | 12/1992 | Quedens et al. ...................... 600/376 |
| 5,178,144 | 1/1993 | Cartmell . |
| 5,197,472 | 3/1993 | Disabito . |
| 5,373,843 | 12/1994 | Quedens et al. . |
| 5,402,780 | 4/1995 | Faasse, Jr. . |
| 5,404,876 * | 4/1995 | DiSabito et al. ...................... 600/376 |
| 5,665,477 | 9/1997 | Meathrel et al. . |
| 5,671,736 * | 9/1997 | Pettit et al. ........................... 600/376 |
| 5,680,859 * | 10/1997 | Urion et al. .......................... 600/376 |
| 5,813,981 | 9/1998 | Carim . |
| 6,151,520 * | 11/2000 | Combs ................................. 600/376 |

OTHER PUBLICATIONS

"Life ♥ Trace™ Disposable Leg Plate", Medical Products, 189 Van Rensselaer Street, Buffalo, NY 14210, ©1994 Graphic Controls Corporation.

Exhibit A —Photographs and Instruction Sheet on Redy-Plate® Disposable Leg Plate, Medical Accessories, Inc., 92 Youngs Rd., Trenton, NJ 08619.

* cited by examiner

Primary Examiner—Linda C. M. Dvorak
Assistant Examiner—David M. Ruddy
(74) Attorney, Agent, or Firm—Lathrop & Clark LLP

(57) ABSTRACT

A body electrode and connector for a fetal electrode has an electrically insulated substrate with an electrical contact strip on the lower surface and two electrical contact strips on the upper surface. An electrically conductive hydrogel layer extends beneath the lower contact strip and adheres to the mother's skin and makes electrical contact with the lower strip, forming a body electrode. Two parallel, but non-engaging, regions of electrically conductive adhesive are disposed over the two upper surface contact strips. The adhesive regions are, in turn, covered by resilient foam strips. Prior to use, the front portions of the electrically conductive adhesive regions are kept from adhesive engagement with the foam strips by removable release liners. The device is deployed by removing a hydrogel-covering release liner and attaching the device to the inner thigh or lower abdomen of the mother. The twisted wire pair from the fetal electrode is extended from the fetus through the birth canal to the mounted device. The release liners are removed from between the foam strips and the substrate and the foam strips are folded back while the two leads from the fetal electrode wire pair are positioned, one lead on each electrically conductive adhesive region, to thereby independently make contact with a respective contact strip. The foam strips are pressed down to securely hold the leads in place. The contacts are positioned to be received within an electrical connector which extends to a fetal heart rate monitor.

12 Claims, 2 Drawing Sheets

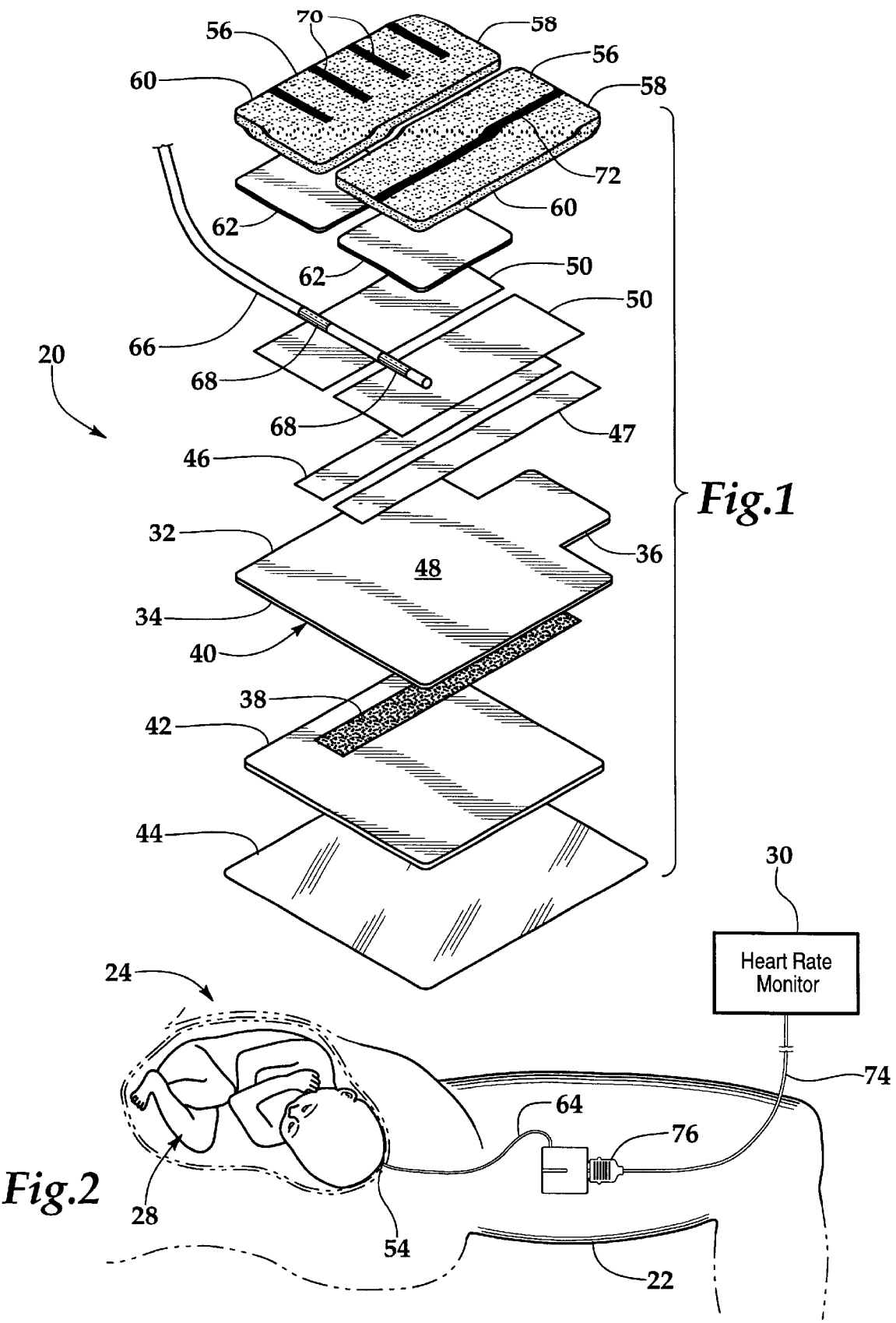

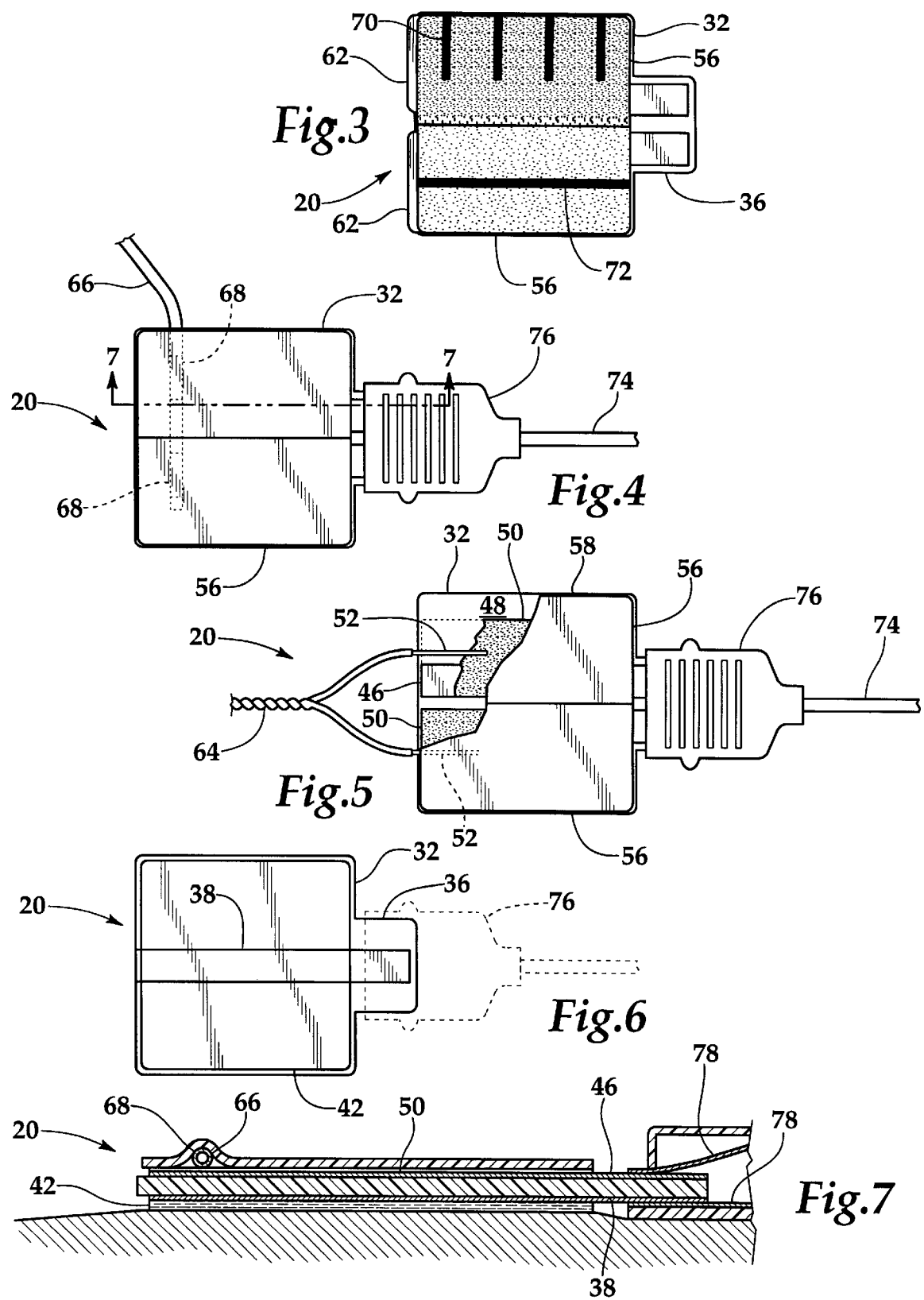

LEG PLATE

CROSS REFERENCES TO RELATED APPLICATIONS

STATEMENT AS TO RIGHTS TO INVENTIONS MADE UNDER FEDERALLY SPONSORED RESEARCH AND DEVELOPMENT

BACKGROUND OF THE INVENTION

The present invention relates to electrical connectors in general, and more particularly to disposable devices for connecting the leads of medical sensors.

The condition and disposition of the infant in the late stages of labor can give important signals to medical personnel concerning the appropriate steps to safely deliver the baby. In some situations, a continuous readout of the infant's heart rate is provided in the time leading up to birth. By reference to this information, the doctor can make a determination as to whether to go ahead with a particular course of action, or whether specialized procedures are called for.

In one common technique, a fetal electrode, such as the one disclosed in U.S. Pat. No. Re. 28,990, is attached to the fetal epidermis, with a twisted pair of wires leading out to an electrode which is strapped or adhesively attached to the mother's leg or abdomen. The electrical signals from the single electrode on the mother's skin and the two wires from the fetal electrode are then conducted through a cable to an electronic processor, known as a fetal heart rate monitor, which determines the instantaneous heart rate of the fetus based on the inputs of the three electrical signals.

Because it is important that the heart rate information not be interrupted at a critical period in the course of labor, the wire leads from the fetal electrode should be securely attached to the body electrode mounted to the mother. Moreover, for the convenience and comfort of the mother, and the expedient treatment by the medical personnel, the attachment of the leads should not require advanced technical skill and should take little time to complete.

A number of devices which satisfy some of these demands are available on the market. However, many of them employ injection molded parts, solder joints, mechanical attachments, and the like which add to the cost of each unit. Because of the time and expense required to clean or sterilize any medical device, it is particularly desirable that devices which come in close contact with patient body fluids be disposable. Hence a device which would securely retain the leads from the fetal electrode, be easy to apply, and be of low-cost, would be very desirable.

SUMMARY OF THE INVENTION

The leg plate of the present invention is economically produced in a continuous sheet or web converting operation. The device has an electrically insulative polyester substrate with a first contact strip adhered to the underside of the substrate. An electrically conductive hydrogel layer extends beneath the first contact strip and serves to adhesively attach the device to the skin of a mother in labor. The hydrogel also makes electrical contact between the mother's skin and the first contact strip forming a body electrode. The hydrogel layer is covered with a peel away plastic release liner until ready for use. Two contact strips are affixed to the upper surface of the substrate and are spaced from one another sidewardly to be electrically insulated from one another. Two parallel, but non-engaging, regions of electrically conductive adhesive are disposed over the two upper surface contact strips. The adhesive regions are, in turn, covered by resilient foam strips. Prior to use, the front portions of the electrically conductive adhesive regions are kept from adhesive engagement with the foam strips by removable release liners. The device is deployed by removing the release liner from the hydrogel and attaching the device to the inner thigh or lower abdomen of the mother. The twisted wire pair from the fetal electrode is extended from the fetus through the birth canal to the mounted device. The release liners are removed from between the foam strips and the substrate and the foam strips are folded back while the two leads from the fetal electrode wire pair are positioned, one lead on each electrically conductive adhesive region, to thereby independently make contact with a respective contact strip. The foam strips are provided with a downwardly facing adhesive and are pressed downward onto the positioned leads to securely hold the leads in place. The two contact strips on the tipper surface, and the single contact strip on the lower surface of the substrate extend onto the connection tab, uncoated with adhesive, where they are positioned to be received within an electrical connector which extends to a fetal heart rate monitor.

The device is equally suited to receive the fetal electrode leads which have been mounted in a single connector having two axially spaced ring contacts. The foam strips may be provided with indicia which direct the user in properly positioning such a single connector.

It is an object of the present invention to provide a leg plate which is of low-cost.

It is also an object of the present invention to provide a leg plate which can alternatively receive bare leads or a braided wire having a plug type connector with two ring contacts, extending from the fetal electrode.

It is another object of the present invention to provide a leg plate device which may be manufactured in a continuous sheet or web conversion process.

It is an additional object of the present invention to provide a leg plate with connectors which is simple to use, and requires minimal training.

Further objects, features and advantages of the invention will be apparent from the following detailed description when taken in conjunction with the accompanying drawings.

BRIEF DESCRIPTION OF THE DRAWINGS

FIG. 1 is an exploded isometric view of the leg plate of this invention.

FIG. 2 is a schematic view of the device of FIG. 1 mounted to the leg of a mother with a lead extending to a contact on the fetus's scalp.

FIG. 3 is a top plan view of the device of FIG. 1 with printed markings illustrated to aid the user in correct lead attachment.

FIG. 4 is a top plan view of the device of FIG. 1 showing a multi-contact plug type connector lead attached, and a cable connector positioned.

FIG. 5 is a top plan view, partially broken away in section, of the device of FIG. 1 showing a cable with two leads attached to the device.

FIG. 6 is a bottom plan view of the device of FIG. 1.

FIG. 7 is a cross-sectional view of the device of FIG. 4, taken along section line 7—7.

DESCRIPTION OF THE PREFERRED EMBODIMENTS

Referring more particularly to FIGS. 1–7, wherein like numbers refer to similar parts, the individual components of the leg plate 20 of this invention are shown in FIG. 1. The leg plate 20 is composed of an assembly of sheet elements which are readily combined in a continuous process as described more fully below. As shown in FIG. 2, the leg plate 20 is affixed to the abdomen or leg 22 of a pregnant woman 24. The leg plate 20 collects electrical information from the skin of the woman 24, while at the same time serving as a conduit for electrical signals conveyed along a cable 64 which is secured to the head of the fetus 28. Electrical signals from the woman 24 and fetus 28 pass through the leg plate without being combined and are received by a fetal heart rate monitor 30 which provides a display of utility to monitoring medical personnel. Conventional fetal heart rate monitors are available, for example, from Hewlett Packard Company, or under the brand name COROMETRICS® from GE Marquette Medical Systems division of GE Medical.

The leg plate 20 has a generally rectangular opaque polyester substrate 32. The substrate is approximately two inches on a side and has a square body 34 with a rearwardly extending tongue 36. A first contact strip 38 is adhered to the lower surface 40 of the substrate 32. The first contact strip 38 is composed of a thin film of silver/silver chloride carbon material. The first contact strip 38 extends from the substrate body 34 onto the substrate tongue 36. An electrically conductive hydrogel layer 42 is adhered to the substrate 32, with the contact strip between the hydrogel layer 42 and the substrate 32. A hydrogel is a hydrated cross-linked polymeric system that contains water in an equilibrium state. Hydrogels typically are oxygen permeable and biocompatible, making them a preferred material for skin contact. The hydrogel layer 42 will cause the leg plate 20 to adhere to the skin of the subject. Prior to use, the hydrogel layer 42 is protected from dust and other contaminants by a polyethylene bottom release liner 44. The hydrogel layer 42 is electrically conductive and allows electrical signals to pass from the woman to the first contact strip 38, allowing the leg plate 20 to serve as a body electrode mounted on the mother.

A second contact strip 46 and a third contact strip 47 comprise fetal electrode contact strips which are mounted to the upper surface 48 of the substrate 32. The two contact strips 46, 47 are identical in composition to the first contact strip 38, and extend parallel to one another from the substrate body onto the substrate tongue 36. The second and third contact strips are spaced sidewardly from one another, and are insulated by the substrate against contact with the first contact strip 38.

Two strips of electrically conductive adhesive 50 are positioned on the upper surface 48 of the substrate to overlie the second contact strip 46 and the third contact strip 47. The strips of electrically conductive adhesive 50 extend along the substrate body 34 but do not extend onto the substrate tongue 36, leaving the contact strips 46, 47 exposed and adhesive-free on the tongue 36. The strips of electrically conductive adhesive 50 are spaced from one another and are thus insulated from one another by the substrate itself. However, each strip of electrically conductive adhesive 50 makes electrical contact with one of the contact strips 46, 47 such that an element that makes electrical contact with any portion of the adhesive 50 also makes electrical contact with the underlying contact strip. The strips of electrically conductive adhesive 50 receive the electrical leads 52 extending from a fetal electrode 54 affixed to the fetus 28.

It should be noted that the fetal heart rate monitoring procedure will typically be ongoing and will not be conducted in isolation but will be merely one source of information during the late stages of labor. Because the leg plate may be attached for a period of time, it will be expected that the subject will not remain entirely at rest. It is therefore of importance that the fetal electrode leads 52 be securely grasped by the leg plate, and that the electrical connection be as extensive as possible.

The mechanical connection between the fetal electrode leads 52 and the electrically conductive adhesive strips 50 is aided by two flexible foam members 56. The flexible foam members 56 are coated with an adhesive and are adhered to the substrate 32 along the rear half 58 of the substrate forward of the substrate tongue 36. To improve the electrical connection between the leads and the device 20, the adhesive on the underside of the flexible foam members 56 may also be electrically conductive. The front half 60 of each flexible foam member 56 is kept from adhesive contact with the substrate until time of use by a release liner 62, which is coated on both sides with a silicone release material such that the release liner 62 is readily separated from both the adhesive underside of the foam member 56 and the conductive adhesive strip 50. As shown in FIG. 3, the release liners 62 protrude frontwardly from the substrate 32 and the overlying foam members 56 to permit them to be readily grasped and removed at time of use. For ease of manufacture, portions of the foam overlying the protruding release liner portions may be retained.

When it is desired to monitor a fetal heart rate, the fetal electrode, of a conventional type, is attached to the fetus within the mother's womb. A braided cable 64 extends from the fetal electrode, and is terminated by two electrical leads 52. The leg plate 20 will preferably be stored in a sealed package which is opened immediately prior to application. The front halves 60 of the two flexible foam members 56 are folded back and the release liners are removed to expose the electrically conductive adhesive layers 50. The two leads 52 are then pressed onto the adhesive layers 50 above the substrate 32, and the foam members 56 are folded back over the adhered leads 52 and pressed into place. The leg plate 20 thus also serves as a fetal electrode receptor.

As shown in FIGS. 4 and 5, there are two common terminations of the fetal electrode cable 64. In the plug type connector 66, such as disclosed in U.S. Pat. No. 5,373,843, and shown in FIG. 1 and FIG. 4, both leads 52 extend along a common axis and are terminated by two spaced conductive rings 68 which are separated by an insulator. The plug type connector 66 is connected to the leg plate 20 by positioning the coaxial leads perpendicular to the second contact strip 46 and the third contact strip 47, such that each conductive ring 68 is positioned over a corresponding electrically conductive adhesive strip.

Another common termination to the braided cable 64 is two bare strips of wire, as shown in FIG. 5. Each strip serves as a lead 52. With this type of termination, the individual leads 52 are inserted parallel to the contact strips 46, 47, one lead for each contact strip.

As shown in FIG. 3, the flexible foam members 56 may be imprinted with indicia 70, 72 to aid the technician in attaching the leads 52. The first indicia 70 may comprise a series of parallel bars extending from the left edge of the leg plate 20 and terminating about two-thirds of the way across the left foam member 56. The first indicia 70 is a visual indicator to the technician to install the plug type connector 66 from the left side to preserve the correct polarity of the leads. The second indicia 72 is provided on the right flexible foam member 56 and is a single bar which extends along the full length of the foam member 56 and is parallel to the foam member. The second indicia 72 shows the maximum insertion of the plug type connector 66. The second indicia 72 is helpful to avoid positioning of the plug type connector in such a way that both conductive rings overlie a single contact strip. To further help the technician distinguish between conductive and nonconductive regions on the substrate, the substrate 32 is preferably formed of a material which has a color which contrasts with the color of the electrically conductive adhesive strips. Typically, the electrically conductive adhesive strips will be black, with optimal visual contrast achieved by utilizing a white polyester substrate.

As shown in FIG. 7, the leg plate 20 is connected to the heart rate monitor 30 through a monitor cable 74 which is terminated by a spring connector 76. The spring connector 76 has three metal contacts 78, two above, and one below, which engage with the second and third contract strips 46, 47 and the first contact strip 38 respectively where the leg plate contact strips extend onto the substrate tongue 36. The substrate 32 itself is always interposed between the contact strips above the substrate and the single contact strip below the substrate, and also serves to prevent electrical connection between the upper and lower metal contacts 78 within the spring connector 76. The spring connector 76 is preferably spring-loaded and disposed in a closed position which is overcome by grasping a pivotable member to open the jaws of the spring connector 76 to permit the insertion of the leg plate contact strips on the substrate tongue. The spring connector 76 will typically be a reusable part and may be provided with a conventional 12-pin connector for interface with conventional fetal heart rate monitors.

With the fetal electrode leads and the spring connector engaged with the leg plate 20, the bottom release linear 44 is peeled away to reveal the hydrogel layer 42 which is pressed into firm engagement with the skin of the mother 24. By being affixed to the mother 24, the leg plate 20 helps to prevent any stresses on the monitor cable from tending to pull the fetal electrode from the baby within the womb.

It should be noted that the device 20, by omitting all molded or machined parts, is particularly well-suited to low-cost manufacture in a continuous process involving various steps of transferring elements from peel away backing release liners. A low-cost part is well-suited to being a disposable, single use, product. In medical applications, disposable units, because they are not reused, have the advantage that they do not require cleaning or sterilization.

In a continuous conversion operation, the leg plate 20 may be assembled by beginning with a polyester substrate web, and applying to the underside of the substrate the first contact strip. The contact strips may be supplied on a peel away release liner, and may be pre-coated with adhesive such that the contact strip transfers to the substrate web when pressed against the substrate web. Alternatively, the contact strips may be applied to the substrate through conventional printing techniques using conductive ink, such as is used in ribbon connectors. The second and third contact strips may be applied to the opposite surface of the substrate in a similar fashion either at the same stage, or at a later stage. Next, the hydrogel layer, supported on its underlying release liner, is adhered to the substrate over the first contact strip. The electrically conductive adhesive regions may also be supplied on release backing material allowing the preshaped regions of adhesive to be readily transferred to the top surface of the substrate. To complete the leg plate, the flexible foam members with underlying release liners are brought into engagement with the electrically conductive adhesive regions.

The final assemblies may then be separated and hygienically packaged. The leg plate 20 thus has no elements that pass through the substrate, thereby requiring no holes to be punched or cut in the substrate, and no elements to be filled within any holes.

It should be noted that, although the substrate has been illustrated as generally rectangular in outline, it could be formed in other shapes, such as square or circular.

It is understood that the invention is not limited to the particular construction and arrangement of parts herein illustrated and described, but embraces such modified forms thereof as come within the scope of the following claims.

I claim:

1. A fetal electrode receptor and body electrode comprising:
    an electrically conductive hydrogel layer facing downwardly;
    a first contact strip positioned above and engaging the hydrogel layer;
    an electrically insulative substrate positioned above the first contact strip, and having an upper surface, wherein the substrate has a protruding tab;
    a second contact strip mounted to the upper surface of the substrate above the first contact strip and electrically insulated from the first contact strip by the substrate;
    a third contact strip mounted to the upper surface of the substrate and electrically insulated from the first contact strip, the third contact strip being spaced from and electrically insulated from the second contact strip;
    a first region of electrically conductive adhesive positioned on the upper surface of the substrate to overlie the second contact strip and to be in electrical connection with the second contact strip;
    a second region of electrically conductive adhesive positioned on the upper surface of the substrate to overlie the third contact strip and to be in electrical connection with the third contact strip, wherein the second region of electrically conductive adhesive is spaced from the first region of electrically conductive adhesive and is electrically insulated therefrom by the substrate; and
    at least one flexible foam member positioned to overlie the second contact strip and the third contact strip, wherein the first contact strip, the second contact strip, and the third contact strip extend along the substrate at the tab and are thereby positioned to be received within an electrical connector, the second contact strip and third contact strip being positioned to receive the electrical leads from a fetal electrode.

2. The device of claim 1 further comprising at least one release liner positioned between portions of the at least one flexible foam member and the regions of electrically conductive adhesive on the upper surface of the substrate, the at least one release liner being removable to permit said flexible foam member portions to be adhered to said electrically conductive adhesive.

3. The device of claim 1 further comprising indicia formed on an upper surface of said at least one flexible foam member to indicate functional orientation of the fetal electrode leads, said leads having two axially spaced ring contacts.

4. The device of claim 1 wherein the substrate comprises an opaque plastic material of contrasting color to the first region of electrically conductive adhesive and the second region of electrically conductive adhesive, to provide visual distinction between the electrically conductive regions and the insulative substrate region and placement of fetal electrode leads having axially spaced ring contacts.

5. The device of claim 1 wherein the flexible foam member has a lower surface with an electrically conductive adhesive disposed thereon.

6. The device of claim 1 wherein the contact strips are formed of conductive ink printed on the substrate.

7. A fetal electrode receptor and body electrode comprising:

an electrically conductive skin attachment layer facing downwardly;

a first contact strip positioned above and engaging the attachment layer;

an electrically insulative substrate positioned above the first contact strip, and having an upper surface;

a second contact strip mounted to the upper surface of the substrate above the first contact strip and electrically insulated from the first contact strip;

a third contact strip mounted to the upper surface of the substrate and electrically insulated from the first contact strip, the third contact strip being spaced from and electrically insulated from the second contact strip, the second contact strip and the third contact strip being thereby positioned to receive the leads from a fetal electrode;

a first region of electrically conductive adhesive positioned on the upper surface of the substrate to make electrical contact with the second contact strip;

a second region of electrically conductive adhesive positioned on the upper surface of the substrate to make electrical contact with the third contact strip, wherein the second region of electrically conductive adhesive is spaced from the first region of electrically conductive adhesive and is electrically insulated therefrom; and at least one overlying member positioned to overlie the second contact strip and the third contact strip, and to thereby engage and retain the leads of a fetal electrode in engagement with the first and second regions of electrically conductive adhesive, and wherein the first contact strip is positioned below the second contact strip and the third contact strip at a connection location, the first contact strip being insulated against electrical contact with the second contact strip and the third contact strip by the intervening substrate.

8. The device of claim 7 further comprising at least one release liner positioned between portions of the at least one overlying member and the regions of electrically conductive adhesive on the upper surface of the substrate, the at least one release liner being removable to permit said overlying member portions to be adhered to said electrically conductive adhesive.

9. The device of claim 7 further comprising indicia formed on an upper surface of said at least one overlying member to indicate functional orientation of the fetal electrode leads, said leads having two axially spaced ring contacts.

10. The device of claim 7 wherein the substrate comprises an opaque plastic material of contrasting color to the first region of electrically conductive adhesive and the second region of electrically conductive adhesive, to provide visual distinction between the electrically conductive regions and the insulative substrate region and placement of fetal electrode leads having axially spaced ring contacts.

11. The device of claim 7 wherein the overlying member has a lower surface with an electrically conductive adhesive disposed thereon.

12. The device of claim 7 wherein the contact strips are formed of conductive ink printed on the substrate.

* * * * *